(12) United States Patent
Viola

(10) Patent No.: US 7,513,877 B2
(45) Date of Patent: Apr. 7, 2009

(54) TISSUE SAMPLING AND REMOVAL APPARATUS AND METHOD

(75) Inventor: Frank J. Viola, Sandy Hook, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 1101 days.

(21) Appl. No.: 10/859,693

(22) Filed: Jun. 3, 2004

(65) Prior Publication Data

US 2004/0225229 A1    Nov. 11, 2004

Related U.S. Application Data

(63) Continuation of application No. 09/988,888, filed on Nov. 19, 2001, now Pat. No. 6,860,860.

(60) Provisional application No. 60/253,147, filed on Nov. 27, 2000.

(51) Int. Cl.
A61B 10/00 (2006.01)
A61B 17/32 (2006.01)
(52) U.S. Cl. .................. 600/564; 600/568; 606/167
(58) Field of Classification Search ............ 600/562, 600/564–568; 606/167, 170, 171
See application file for complete search history.

(56) References Cited

U.S. PATENT DOCUMENTS

| 737,293 | A | 8/1903 | Summerfeldt |
| 1,167,014 | A | 1/1916 | O'Brien |
| 1,255,330 | A | 2/1918 | Morgan et al. |
| 1,585,934 | A | 5/1926 | Muir |
| 1,663,761 | A | 3/1928 | Johnson |
| 1,867,624 | A | 7/1932 | Hoffman |
| 2,505,358 | A | 4/1950 | Gusberg et al. |
| 2,705,949 | A | 4/1955 | Silverman |
| 2,729,210 | A | 1/1956 | Spencer |
| 2,919,692 | A | 1/1960 | Ackerman |
| 3,400,708 | A | 9/1968 | Scheidt |
| 3,477,423 | A | 11/1969 | Griffith |
| 3,561,429 | A | 2/1971 | Jewett et al. |
| 3,590,808 | A | 7/1971 | Muller |
| 3,606,878 | A | 9/1971 | Kellogg, Jr. |

(Continued)

FOREIGN PATENT DOCUMENTS

DE    935625    11/1955

(Continued)

OTHER PUBLICATIONS

Brochure—"ASAP Automatic Soft Tissue Biopsy System" (2 pages) (Published before filing date Nov. 19, 2001).

(Continued)

Primary Examiner—Max Hindenburg
Assistant Examiner—Jonathan M Foreman

(57) ABSTRACT

A tissue sampling device (10) for retrieving one or more tissue samples from a patient is either handheld or mounted to a moveable carriage (184) and advanced so that the needle tip (152) is introduced into the patient. The needle tip (152) is advanced until the tissue receiving basket (154) reaches the tissue sample target zone (190). Vacuum pressure is supplied to the basket (154) via a vacuum tube (144) so that tissue to be sampled is drawn into the basket (154). The cutter (42) is rotated and advanced linearly to cut a tissue sample (212) which is then retrieved by retracting the needle (40).

20 Claims, 4 Drawing Sheets

U.S. PATENT DOCUMENTS

| | | |
|---|---|---|
| 3,732,858 A | 5/1973 | Banko |
| 3,734,099 A | 5/1973 | Bender et al. |
| 3,844,272 A | 10/1974 | Banko |
| 3,929,123 A | 12/1975 | Jamshidi |
| 3,989,033 A | 11/1976 | Halpern et al. |
| 3,995,619 A | 12/1976 | Glatzer |
| 4,099,518 A | 7/1978 | Baylis et al. |
| 4,200,106 A | 4/1980 | Douvas et al. |
| 4,203,444 A | 5/1980 | Bonnell et al. |
| 4,210,146 A | 7/1980 | Banko |
| 4,220,155 A | 9/1980 | Kimberling et al. |
| 4,243,048 A | 1/1981 | Griffin |
| 4,246,902 A | 1/1981 | Martinez |
| 4,274,414 A | 6/1981 | Johnson et al. |
| 4,282,884 A | 8/1981 | Boebel |
| 4,306,570 A | 12/1981 | Matthews |
| 4,314,560 A | 2/1982 | Helfgott et al. |
| 4,340,066 A | 7/1982 | Shah |
| 4,396,021 A | 8/1983 | Baumgartner |
| 4,403,617 A | 9/1983 | Tretinyak |
| 4,461,305 A | 7/1984 | Cibley |
| 4,513,745 A | 4/1985 | Amoils |
| 4,517,977 A | 5/1985 | Frost |
| 4,530,356 A | 7/1985 | Helfgott et al. |
| 4,577,629 A | 3/1986 | Martinez |
| 4,589,414 A | 5/1986 | Yoshida et al. |
| 4,598,710 A | 7/1986 | Kleinberg et al. |
| 4,600,014 A | 7/1986 | Beraha |
| 4,603,694 A | 8/1986 | Wheeler |
| 4,643,196 A | 2/1987 | Tanaka et al. |
| 4,644,951 A | 2/1987 | Bays |
| 4,651,752 A | 3/1987 | Fuerst |
| 4,651,753 A | 3/1987 | Lifton |
| 4,660,267 A | 4/1987 | Wheeler |
| 4,662,869 A | 5/1987 | Wright |
| 4,667,684 A | 5/1987 | Leigh |
| 4,669,496 A | 6/1987 | Kemp et al. |
| 4,674,502 A | 6/1987 | Imonti |
| 4,678,459 A | 7/1987 | Onik et al. |
| 4,681,123 A | 7/1987 | Valtchev |
| 4,685,458 A | 8/1987 | Leckrone |
| 4,696,298 A | 9/1987 | Higgins et al. |
| 4,699,154 A | 10/1987 | Lindgren |
| 4,702,260 A | 10/1987 | Wang |
| 4,702,261 A | 10/1987 | Cornell et al. |
| 4,708,147 A | 11/1987 | Haaga |
| 4,711,250 A | 12/1987 | Gilbaugh, Jr. et al. |
| 4,733,662 A | 3/1988 | DeSatnick et al. |
| 4,733,671 A | 3/1988 | Mehl |
| 4,735,215 A | 4/1988 | Goto et al. |
| 4,776,346 A | 10/1988 | Beraha et al. |
| 4,781,186 A | 11/1988 | Simpson et al. |
| 4,781,202 A | 11/1988 | Janese |
| 4,799,494 A | 1/1989 | Wang |
| 4,819,635 A | 4/1989 | Shapiro |
| 4,838,280 A | 6/1989 | Haaga |
| 4,844,088 A | 7/1989 | Kambin |
| 4,850,354 A | 7/1989 | McGurk-Burleson et al. |
| 4,850,373 A | 7/1989 | Zatloukal et al. |
| 4,874,375 A | 10/1989 | Ellison |
| 4,881,551 A | 11/1989 | Taylor |
| 4,893,635 A | 1/1990 | de Groot et al. |
| 4,907,599 A | 3/1990 | Taylor |
| 4,917,100 A | 4/1990 | Nottke |
| 4,919,146 A | 4/1990 | Rhinehart et al. |
| 4,924,878 A | 5/1990 | Nottke |
| 4,936,835 A | 6/1990 | Haaga |
| RE33,258 E | 7/1990 | Onik et al. |
| 4,940,061 A | 7/1990 | Terwilliger et al. |
| 4,944,308 A | 7/1990 | Akerfeldt |
| 4,950,265 A | 8/1990 | Taylor |
| 4,953,558 A | 9/1990 | Akerfeldt |
| 4,958,625 A | 9/1990 | Bates et al. |
| 4,976,269 A | 12/1990 | Mehl |
| 4,982,739 A | 1/1991 | Hemstreet et al. |
| 4,989,614 A | 2/1991 | Dejter, Jr. et al. |
| 4,991,592 A | 2/1991 | Christ |
| 4,991,600 A | 2/1991 | Taylor |
| 5,000,745 A | 3/1991 | Guest et al. |
| 5,002,553 A | 3/1991 | Shiber |
| RE33,569 E | 4/1991 | Gifford, III et al. |
| 5,005,585 A | 4/1991 | Mazza |
| 5,006,114 A | 4/1991 | Rogers et al. |
| 5,009,391 A | 4/1991 | Steigerwald |
| 5,009,659 A | 4/1991 | Hamlin et al. |
| 5,011,473 A | 4/1991 | Gatturna |
| 5,011,490 A | 4/1991 | Fischell et al. |
| 5,012,818 A | 5/1991 | Joishy |
| 5,014,717 A | 5/1991 | Lohrmann |
| 5,018,530 A | 5/1991 | Rank et al. |
| 5,019,036 A | 5/1991 | Stahl |
| 5,019,088 A | 5/1991 | Farr |
| 5,019,089 A | 5/1991 | Farr |
| 5,021,059 A | 6/1991 | Kensey et al. |
| 5,026,384 A | 6/1991 | Farr et al. |
| 5,027,827 A | 7/1991 | Cody et al. |
| 5,031,634 A | 7/1991 | Simon |
| 5,035,248 A | 7/1991 | Zinnecker |
| 5,036,860 A | 8/1991 | Leigh et al. |
| 5,040,715 A | 8/1991 | Green et al. |
| 5,041,129 A | 8/1991 | Hayhurst et al. |
| 5,047,008 A | 9/1991 | de Juan, Jr. et al. |
| 5,047,040 A | 9/1991 | Simpson et al. |
| 5,048,538 A | 9/1991 | Terwilliger et al. |
| 5,053,014 A | 10/1991 | Van Heugten |
| 5,053,044 A | 10/1991 | Mueller et al. |
| 5,056,529 A | 10/1991 | de Groot |
| 5,057,082 A | 10/1991 | Burchette, Jr. |
| 5,057,085 A | 10/1991 | Kopans |
| 5,059,197 A | 10/1991 | Urie et al. |
| 5,060,658 A | 10/1991 | Dejter, Jr. et al. |
| 5,061,281 A | 10/1991 | Mares et al. |
| 5,074,311 A | 12/1991 | Hasson |
| 5,074,841 A | 12/1991 | Ademovic et al. |
| 5,074,871 A | 12/1991 | Groshong |
| 5,078,142 A | 1/1992 | Sixzek et al. |
| 5,078,723 A | 1/1992 | Dance et al. |
| 5,080,655 A | 1/1992 | Haaga |
| 5,085,659 A | 2/1992 | Rydell |
| 5,087,265 A | 2/1992 | Summers |
| 5,090,419 A | 2/1992 | Palestrant |
| 5,092,873 A | 3/1992 | Simpson et al. |
| 5,106,364 A | 4/1992 | Hayafuji et al. |
| 5,111,828 A | 5/1992 | Kornberg et al. |
| 5,121,751 A | 6/1992 | Panalletta |
| 5,125,413 A | 6/1992 | Baran |
| 5,127,419 A | 7/1992 | Kaldany |
| 5,133,359 A | 7/1992 | Kedem |
| 5,133,360 A | 7/1992 | Spears |
| 5,135,481 A | 8/1992 | Nemeh |
| RE34,056 E | 9/1992 | Lindgren et al. |
| 5,146,921 A | 9/1992 | Terwilliger et al. |
| 5,152,744 A | 10/1992 | Krause et al. |
| 5,156,160 A | 10/1992 | Bennett |
| 5,161,542 A | 11/1992 | Palestrant |
| 5,174,300 A | 12/1992 | Bales et al. |
| 5,176,628 A | 1/1993 | Charles et al. |
| 5,178,625 A | 1/1993 | Groshong |
| 5,183,052 A | 2/1993 | Terwilliger |
| 5,183,054 A | 2/1993 | Burkholder et al. |
| 5,188,118 A | 2/1993 | Terwilliger |
| 5,192,291 A | 3/1993 | Pannek, Jr. |
| 5,195,533 A | 3/1993 | Chin et al. |
| 5,195,988 A | 3/1993 | Haaga |

| | | | |
|---|---|---|---|
| 5,197,484 A | 3/1993 | Kornberg et al. |
| 5,199,441 A | 4/1993 | Hogle |
| 5,211,651 A | 5/1993 | Reger et al. |
| 5,213,110 A | 5/1993 | Kedem et al. |
| 5,217,458 A | 6/1993 | Parins |
| 5,217,479 A | 6/1993 | Shuler |
| 5,222,966 A | 6/1993 | Perkins et al. |
| 5,224,470 A | 7/1993 | Schnepp-Pesch et al. |
| 5,224,488 A | 7/1993 | Neuffer |
| 5,224,945 A | 7/1993 | Pannek, Jr. |
| 5,226,909 A | 7/1993 | Evans et al. |
| 5,226,910 A | 7/1993 | Kajiyama et al. |
| 5,234,000 A | 8/1993 | Hakky et al. |
| 5,234,994 A | 8/1993 | Shiraki et al. |
| 5,236,334 A | 8/1993 | Bennett |
| 5,242,460 A | 9/1993 | Klein et al. |
| 5,243,994 A | 9/1993 | Ranaletta |
| 5,249,582 A | 10/1993 | Taylor |
| 5,249,583 A | 10/1993 | Mallaby |
| 5,250,059 A | 10/1993 | Andreas et al. |
| 5,250,065 A | 10/1993 | Clement et al. |
| 5,251,641 A | 10/1993 | Xavier |
| 5,254,105 A | 10/1993 | Haaga |
| 5,269,793 A | 12/1993 | Simpson |
| 5,269,797 A | 12/1993 | Bonati et al. |
| 5,269,798 A | 12/1993 | Winkler |
| 5,273,051 A | 12/1993 | Wilk |
| 5,273,519 A | 12/1993 | Koros et al. |
| 5,275,609 A | 1/1994 | Pingleton et al. |
| 5,282,476 A | 2/1994 | Terwilliger |
| 5,282,484 A | 2/1994 | Reger |
| 5,284,156 A | 2/1994 | Schramm et al. |
| 5,285,795 A | 2/1994 | Ryan et al. |
| 5,286,253 A | 2/1994 | Fucci |
| 5,290,303 A | 3/1994 | Pingleton et al. |
| 5,292,310 A | 3/1994 | Yoon |
| 5,301,684 A | 4/1994 | Ogirala |
| 5,306,260 A | 4/1994 | Kanner |
| 5,312,425 A | 5/1994 | Evans et al. |
| 5,313,958 A | 5/1994 | Bauer |
| 5,316,013 A | 5/1994 | Striebel, II et al. |
| 5,320,110 A | 6/1994 | Wang |
| 5,324,300 A | 6/1994 | Elias et al. |
| 5,335,671 A | 8/1994 | Clement |
| 5,336,176 A | 8/1994 | Yoon |
| 5,353,804 A | 10/1994 | Kornberg et al. |
| 5,366,463 A | 11/1994 | Ryan |
| 5,366,464 A | 11/1994 | Belknap |
| 5,366,468 A | 11/1994 | Fucci et al. |
| 5,368,045 A | 11/1994 | Clement et al. |
| 5,392,790 A | 2/1995 | Kanner et al. |
| 5,394,887 A | 3/1995 | Haaga |
| 5,403,334 A | 4/1995 | Evans et al. |
| 5,409,013 A | 4/1995 | Clement |
| 5,415,182 A | 5/1995 | Chin et al. |
| 5,417,703 A | 5/1995 | Brown et al. |
| 5,419,774 A | 5/1995 | Willard et al. |
| 5,425,376 A | 6/1995 | Banys et al. |
| 5,437,630 A | 8/1995 | Daniel et al. |
| 5,439,474 A | 8/1995 | Li |
| 5,449,001 A | 9/1995 | Terwilliger |
| 5,456,689 A | 10/1995 | Kresch et al. |
| 5,458,112 A | 10/1995 | Weaver |
| 5,476,101 A | 12/1995 | Schramm et al. |
| 5,477,862 A | 12/1995 | Haaga |
| 5,492,130 A | 2/1996 | Chiou |
| 5,501,664 A | 3/1996 | Kaldany |
| 5,505,210 A | 4/1996 | Clement |
| 5,505,211 A | 4/1996 | Ohto et al. |
| 5,507,298 A | 4/1996 | Schramm et al. |
| 5,511,556 A | 4/1996 | DeSantis |
| 5,526,822 A | 6/1996 | Burbank et al. |
| 5,535,755 A | 7/1996 | Heske |
| 5,538,010 A | 7/1996 | Darr et al. |
| 5,546,957 A | 8/1996 | Heske |
| 5,551,442 A | 9/1996 | Kanner et al. |
| 5,560,373 A | 10/1996 | De Santis |
| 5,564,436 A | 10/1996 | Hakky et al. |
| 5,570,699 A | 11/1996 | Kass |
| 5,595,185 A | 1/1997 | Erlich |
| 5,617,874 A | 4/1997 | Baran |
| 5,649,547 A | 7/1997 | Ritchart et al. |
| 5,655,542 A | 8/1997 | Weilandt |
| 5,752,923 A | 5/1998 | Terwilliger |
| 5,769,086 A | 6/1998 | Ritchart et al. |
| 5,775,333 A | 7/1998 | Burbank et al. |
| 5,817,033 A | 10/1998 | DeSantis et al. |
| 5,830,153 A | 11/1998 | Kass |
| 5,842,999 A | 12/1998 | Pruitt et al. |
| 5,849,023 A | 12/1998 | Mericle |
| 5,916,175 A | 6/1999 | Bauer |
| 5,928,164 A | 7/1999 | Burbank et al. |
| 5,944,673 A | 8/1999 | Gregoire et al. |
| 5,964,716 A | 10/1999 | Gregoire et al. |
| 5,980,469 A | 11/1999 | Burbank et al. |
| 5,980,545 A | 11/1999 | Pacala et al. |
| 5,989,197 A | 11/1999 | Avaltroni |
| 5,993,399 A | 11/1999 | Pruitt et al. |
| 6,007,497 A | 12/1999 | Huitema |
| 6,017,316 A | 1/2000 | Ritchart et al. |
| 6,018,676 A | 1/2000 | Davis et al. |
| 6,022,324 A | 2/2000 | Skinner |
| 6,027,458 A | 2/2000 | Janssens |
| 6,086,544 A | 7/2000 | Hibner et al. |
| 6,610,020 B2 | 8/2003 | Voegele |
| 2003/0144605 A1 | 7/2003 | Burbank et al. |

FOREIGN PATENT DOCUMENTS

| | | |
|---|---|---|
| DE | 1 817 555 | 12/1968 |
| EP | 0 010 321 | 10/1979 |
| EP | 0 207 726 | 6/1986 |
| EP | 0 221 007 | 10/1986 |
| EP | 0 238 461 | 2/1987 |
| EP | 0 378 692 | 7/1990 |
| EP | 0 442 851 | 8/1991 |
| EP | 0 536 888 | 4/1993 |
| EP | 0 919 190 A2 | 11/1998 |
| EP | 0 995 400 | 4/2000 |
| FR | 1161400 | 7/1956 |
| FR | 1267960 | 6/1960 |
| FR | 2332743 | 11/1975 |
| SU | 400319 | 2/1974 |
| SU | 400319 | 11/1974 |
| SU | 520976 | 12/1974 |
| SU | 483978 | 12/1975 |
| SU | 707576 | 3/1976 |
| SU | 648219 | 2/1979 |
| SU | 1178422 | 4/1984 |
| SU | 1456115 | 2/1989 |
| SU | 1537233 | 1/1990 |
| SU | 1614800 | 12/1990 |
| WO | WO 83/03343 | 10/1983 |
| WO | WO 105309 | 10/1983 |
| WO | WO 91/01112 | 7/1991 |
| WO | WO 92/00040 | 1/1992 |
| WO | WO 93/12707 | 7/1993 |
| WO | WO 95/25465 | 9/1995 |
| WO | WO 95/27441 | 10/1995 |
| WO | WO 96/24289 | 8/1996 |
| WO | WO 99/15079 | 4/1999 |

WO  WO 00/30546  6/2000

OTHER PUBLICATIONS

Brochure—"When It Comes to Core Samples, I Demand Accuracy and Consistency for All My Patients" (Published before filing date Nov. 19, 2001).

Brochure—Surgical Dynamics Nucleotome System, Automated Percutaneous Lumbar Disectomy 3 pgs. (Published before filing date Nov. 19, 2001).

Brochure—Introducing The Singular Technology for Multi-Core Microcalcification Sampling—5 pages (Published before filing date Nov. 19, 2001).

Biopsys: Mammotome Multi-Probe and Motorized Driver Instructions for Use; 3 pgs.; 1994 Article—"Sterotaxic Needle Core Biopsy of Breat Legions Using a Regular Mammographic Table With An Adaptable Stereotaxic Device" -by Judy S. Caines et al.:AJR163, Aug. 1995; pp. 317-321.

Article—"Sterotactic Breat Biopsy with a Biopsy Gun", by Steve H. Parker, M.D. et al.; reprinted from Radiology, vol. 176,No. 3, pp. 741-747; Sep. 1990.

Article—"Sterotactic Percutaneous Breat Core Biopsy Technical Adaption and Initial Experience" by Captain Jeffrey D. Lovin, M.D. et al.; Breat Dis 1990: 3:135-143.

Article—"Selective Use of Image-Guided Large-Core Needle Biopsy of the Breast: Accuracy and Cost Effectiveness" by Anthony J. Doyle et al., AJR:165; Aug. 1995; pp. 281-284.

Article—"Breat Biopsy: A Comparative Study of Sterotacically Guided Core and Excisional Techniques" by John J. Gisvold et al.; AJR:162; Apr. 1994; pp. 815-820.

Article—"Sterotactic Core Needle Biopsy of Mammographic Breat Lesions As A Viable Alternative to Surgical Biopsy"; by Raoulf A. Mikhail et al.; Annals of Surgical Oncology. 1(5):363:3367; 1994.

TISSUE SAMPLING AND REMOVAL APPARATUS AND METHOD

CROSS-REFERENCE TO RELATED APPLICATION

The present application is a continuation application which claims the benefit of and priority to U.S. application Ser. No. 09/988,888, filed on Nov. 19, 2001, now U.S. Pat. No. 6,860,860 which, in turn, claims the benefit of and priority to U.S. Provisional Application Ser. No. 60/253,147, filed on Nov. 27, 2000, the entire contents of each of which being incorporated herein by reference.

TECHNICAL FIELD

The present invention relates to tissue sample removal and, more particularly, breast tissue biopsy apparatus and procedures.

BACKGROUND OF THE INVENTION

Various known tissue and biopsy removal apparatus and methods exist. Known devices include various types of needle coring and moveable cutter devices. Certain of such devices lack effective cutting ability, the ability to retrieve multiple samples, or versatility in terms of use with a variety of accessories and in a variety of procedures. For example, certain tissue removal devices are limited in terms of their need to be used only with certain types of tables or imaging equipment. Some tables or imaging equipment are expensive or cumbersome. Some tables or imaging equipment are adapted to fit or be used with one or a limited number of models and manufacture of biopsy or tissue retrieval devices.

Some handheld biopsy or tissue retrieval devices exist but lack the effective cutting and tissue retrieving capabilities of more complex, automated devices normally restricted to use with tables and larger assemblies. Certain handheld devices are limited to single tissue sample retrieval operations and must be fully removed before subsequent samples can be taken, thus losing the precise location of a prior sample.

OBJECTS OF THE INVENTION

It is an object of the present invention to provide a tissue removal device and method that have superior cutting ability, the ability to retrieve multiple samples while holding a tissue sample site, and versatility in terms of use with a variety of accessories and in a variety of procedures. It is a further object to provide a tissue removal device and method that may be used with a carriage and table or that may be used in a completely handheld fashion.

These and other objects and advantages that are inherent to the present invention are disclosed herein.

SUMMARY OF THE INVENTION

The present invention is directed to a tissue removal device and method that utilizes a device having a housing that may be handheld or mounted to a carriage used with a conventional biopsy table and imaging system. The tissue removal device has a non-rotatable needle including a vacuum-assisted tissue sample basket and a rotating needle that can be advance or retracted linearly. A single, re-usable drive cable having a drive gear mounted at its end is attached to a remote drive motor. The single drive cable rotates selectively to actuate cutter rotation, advancement and withdrawal, as well as selective needle displacement to retrieve a severed sample and to re-position the needle.

In operation the needle is positioned in a tissue target site so that a vacuum-pressurized basket near the distal end of the needle draws tissue in. The cutter is rotated and advanced past the basket to sever a tissue sample held in the basket. The cutter is then held in position while the needle is retracted in order to locate the tissue basket for tissue removal. The sequence can be repeated as needed until a desired number of tissue samples are removed. The rotational location of subsequent samples can be controlled by rotating the entire device relative to the patient.

The entire device is designed to be detached from the drive cable and discarded.

DESCRIPTION OF THE PREFERRED EMBODIMENTS

Structural Components

Figure 1:
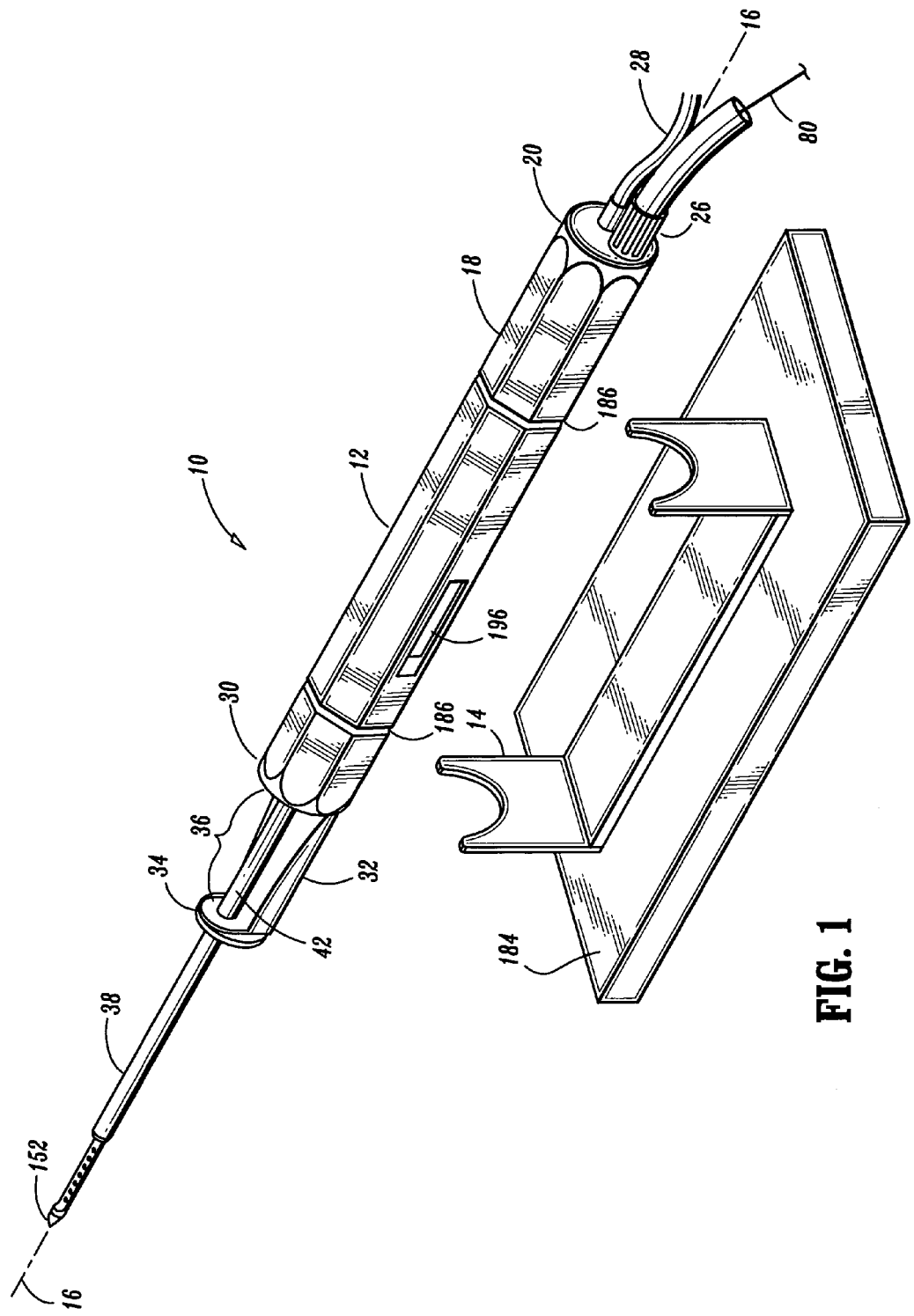
FIG. 1 is a schematic, isometric, partial view of a tissue removal device according to a first embodiment of the present invention.

Referring to FIGS. 1-5, a preferred embodiment of the present invention tissue sampling device is described herein. The device (10) includes a housing (12) shaped in any one of a variety of configurations that is easily hand held or mounted for rotation to another structure such as the cradle (14) shown in FIG. 1. The housing (12) is preferably generally elongated so as to define a longitudinal axis (16) therethrough. The material of the housing (12) may be any one of a variety of materials, including metals or plastics, suitable for use with medical devices and of sufficient strength and stiffness to perform as described herein. Since in the preferred embodiment the entire housing (12) and its inner components are intended to be disposed after use with a single patient, it is desirable that the housing (12) comprise an inexpensive material. The housing (12) of the preferred embodiment is provided with rotational position indicia (18) for locating the housing (12) in selective rotational positions relative to the patient or to the cradle (14), as will be described below.

At the proximal end (20) of the housing (12), a drive cable port (22) and a vacuum port (24) are positioned on the distal end face (25). The drive cable port (22) receives a drive cable end (26) of a drive cable (80) and the vacuum port (24) receives a vacuum conduit (28), the function of each being described below.

The distal end (30) of the housing (12) includes an extension arm (32) and a distal support (34) forming a tissue specimen retrieval zone (36) proximally adjacent to the distal support (34). A radiolucent tube (38) is mounted to the distal end (30) of the housing (12) in a manner permitting adjustable extension distally from the housing (12), as will be described below.

Extending from the distal end (30) of the housing (12), and passing through the distal support (34) are a sampling needle (40) and a rotational cutter (42). The cutter (42) is mounted within the housing (12) in a manner permitting it to move rotationally and axially relative to the housing (12). The needle (40) is mounted within the housing (12) in a manner permitting it to move axially relative to the housing (12), but which prevents relative rotation of the needle (40) relative to the housing (12).

Figure 2:
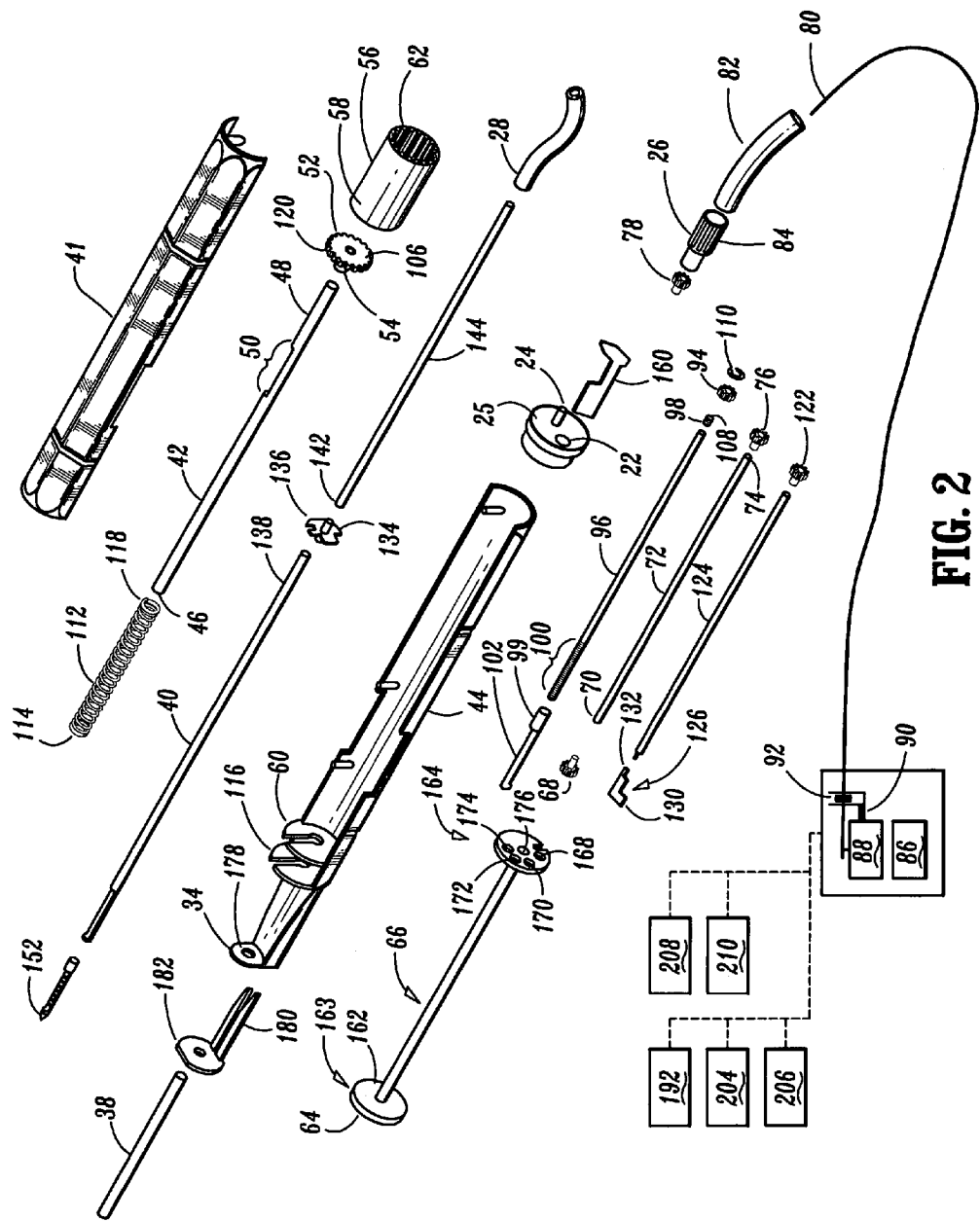
FIG. 2 is a schematic, exploded isometric view of the device shown in FIG. 1.

Referring to the exploded view shown in FIG. 2, the housing (12) comprises a first half (41) and a second half (44), each being adapted to interfit with the other to form a single, enclosed housing (12). The cutter (42) comprises an elongated, hollow tube having a distal end (46) with a sharpened edge for cutting tissue, a proximal end (48), and a tissue sample retrieval window (50) located near the proximal end (48). The cutter (42) is preferably made of a metal or similar rigid material that may be sharpened at the distal end (46) edge for cutting tissue. A first cutter gear (52) is connected to the proximal end (48) of the cutter (42) in a fixed relationship to transmit rotational motion to the cutter (42). The first cutter gear (52) may be connected to the cutter (42) by various suitable means including, as shown, a distal extension (54) that can be welded, press-fit or otherwise attached to the cutter (42).

An internal gear (56) which is mounted inside the housing (12) for rotational movement only transmits rotational motion to the first cutter gear (52) which, in turn, rotates the cutter (42). The first cutter gear (52) and the internal gear (56) are sized so that the first cutter gear (52) is positioned inside the internal gear (56). The number and ratio of gear teeth may vary according to desired output. The first cutter gear (52) is adapted to translate longitudinally inside of the internal gear (56) in order to facilitate advancement or retraction of the cutter (42) in the longitudinal direction relative to the housing (12). The internal gear (56) is mounted in the housing (12) in such a manner that the distal end (58) of the internal gear (56) abuts a first stop plate (60) fixed internally in the housing (12). The proximal end (62) of the internal gear (56) abuts the distal end face (64) of the gear case (66) which is mounted inside the housing (12) in a non-moving manner which will be described below.

Rotational movement of the internal gear (56) which, in turn, drives the first cutter gear (52) and the cutter (42), is caused by rotational motion transmitted directly to it by the second cutter gear (68). The second cutter gear (68) is fixedly mounted directly to the distal end (70) of a cutter drive shaft (72). Fixedly mounted to the proximal end (74) of the cutter drive shaft (72) is a third cutter gear (76). The third cutter gear (76), when driven, transmits rotational motion through the cutter shaft (72) to the second cutter gear (68) and, thus, the internal gear (62), the first cutter gear (52) and, finally, the cutter (42). Rotational motion is imparted on the third cutter gear (76) by the master drive gear (78) which is driven by the drive cable (80) and housed in the cable housing (82) having a cable housing end (84).

The drive cable (80) is rotationally driven by a conventional motor (86) or other drive means located remotely. The drive cable (80) is moved axially relative to the housing (12) by conventional means such as a solenoid or other type of linear actuator (88). The linear actuator (88) may, for example, include a push-pull piston (90) adapted to engage a disc or collar (92) that is crimped or otherwise fastened to the cable (80). By selectively moving the cable (80) and thus the master drive gear (78), the third cutter gear (76) can be selectively engaged or disengaged in order to selectively drive or not drive the cutter (42).

A cutter advance gear (94) is provided and positioned within the housing (12) in such a manner so that it is simultaneously engaged by the master drive gear (78) when the master drive gear (78) engages the third cutter gear (76). The cutter advance gear (94) cooperates with additional components, as described below, which convert the rotational motion of the master drive gear (78) into linear motion in order to extend or retract the cutter (42) in a linear fashion.

The cutter advance gear (94) is connected to a cutter advance shaft (96) by a spring clutch (98) which transmits rotational motion from the gear (92) to the shaft (96) in order to linearly advance or retract a lead nut (99) along a threaded section (100) of the shaft (96). The lead nut (99) has an extension arm (102) that extends distally through the distal end face (64) of the gear case (66) so that the distal end (104) of the extension arm (102) abuts the proximal face (106) of the first cutter gear (52). As the cutter advance shaft (96) is rotated in a first direction, the lead nut (99) translates distally, thereby pushing the first cutter gear (52) and hence the cutter (42) so that they move distally relative to the internal gear (56) and the housing (12). The spring clutch (98) is selected so that it will allow relative slippage between the cutter advance shaft (96) and the cutter advance gear (92) if a predetermined axial resistance force is applied to the cutter (42). The cutter (42) will slow or stop moving in the axial direction, while continuing to rotate, until the resistance is diminished or overcome. An extension flag (108) of the spring clutch (98) and a retaining clip (110) enable it to be connected to the cutter advance gear (92).

Accordingly, reversing the direction of rotation of the master drive gear (78) will, in turn, control the rotational and linear movement direction of the cutter (42) in accordance with the operation of the device as will be described below. When the rotation of the master drive gear (78) is directed to cause the cutter advance gear (92) to rotate in a direction that will result in the lead nut (99) moving toward the proximal direction, a spring (112) biased on its distal end (114) by a second stop plate (116) and on its proximal end (118) by the distal face (120) of the first cutter gear (52) will push the first cutter gear (52) and the cutter (42) back in the proximal direction. The rate of movement in this manner will be dictated by the retreat of the lead nut (99) since it abuts the proximal end (106) of the first cutter gear (52).

Figure 3:
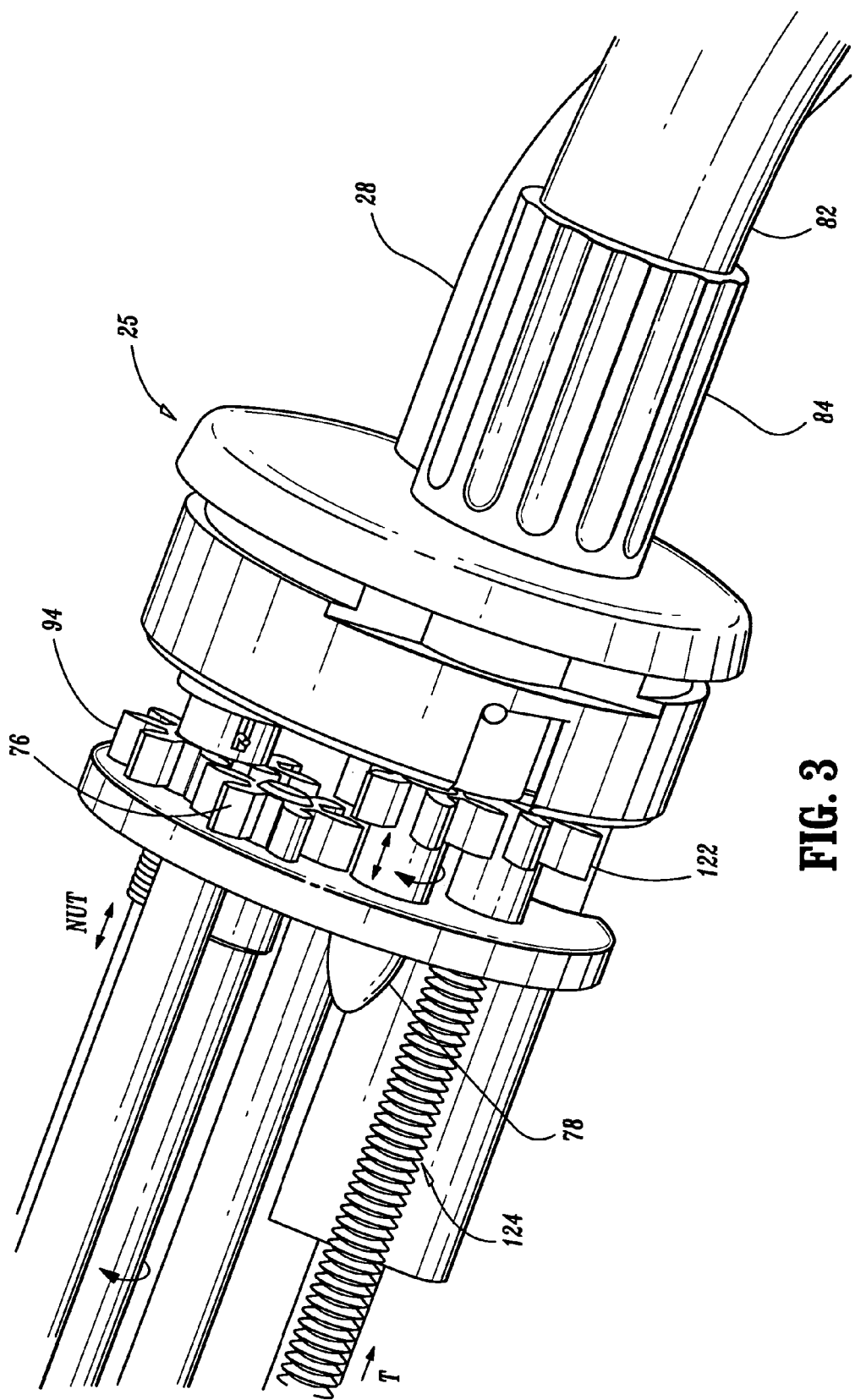
FIG. 3 is a schematic, partial isometric view of the device shown in FIG. 1.

Advancement or retraction of the needle (40) in accordance with operation as described below, is activated by positioning the master drive gear (78) in engagement with the needle drive gear (122). As described above, the master drive gear (78) is moved axially relative to the housing (12) and, thus, can be selectively engaged with the needle drive gear (122). As shown in FIG. 3, the needle drive gear (122) is offset from the third cutter gear (76) and the cutter advance gear (94) so that it can be engaged only when the two latter gears are not engaged, and vice-versa. When the master drive gear (78) engages the needle drive gear (122), rotational motion from the master drive gear (78) is transmitted through the needle drive gear (122) to the needle leadscrew (124) to which the needle drive gear (122) is fixed. The leadscrew (124) is threaded so that, when rotated, it causes a toggle nut (126) having internal threads (128) and positioned thereon to translate linearly along the leadscrew (124). Depending on the direction of rotation of the master drive gear (78), the toggle nut (126) will advance distally or retreat proximally along the leadscrew (124). The toggle nut (126) has two flags (130, 132) that extend generally radially and that are offset from each other axially as shown.

The first flag (130) of the toggle nut (126) is positioned relative to the needle (40) in order to selectively engage the distal end face (134) of the needle flange (136). The needle flange (136) is fixedly attached to the proximal end (138) of the needle (40). The first flag (130) selectively engages or disengages the needle flange (136) by being rotated into or out or axial alignment with a portion of the needle flange (136). When positioned for engagement with the flange (136), the first flag (130) will pull the flange (136) and needle (40) in a retracted, proximal direction as the toggle nut (126) moves proximally along the leadscrew (124) as described above.

The second flag (132) of the toggle nut (126) is positioned relative to the needle (40) in order to selectively engage the proximal end face (135) of the needle flange (136). The needle flange (136) is fixedly attached to the proximal end (138) of the needle (40). The second flag (132) selectively engages or disengages the needle flange (136) by being rotated into or out or axial alignment with a portion of the needle flange (136). When positioned for engagement with the flange (136), the second flag (132) will push the flange (136) and needle (40) in an extended, distal direction as the toggle nut (126) moves distally along the leadscrew (124) as described above.

In addition to being spaced axially with respect to each other, the flags (130, 132) are offset angularly so that the first flag (130), being located distally of the second flag (132), may be positioned for alignment with the flange (136) while the second flag (132) is positioned out of alignment with the flange (136). This facilitates the optional firing mode of the needle (40) that will be described below, by keeping the second flag (132) out of the way of the flange (136) during firing.

The needle (40) and the attached flange (136) are telescopically received over the distal end (142) of the vacuum tube (144) for relative axial movement with respect thereto. The vacuum tube (144) remains fixed with respect to the housing (12) when the needle (40) is moved axially as described above. The proximal end (146) of the vacuum tube (144) is attached to a vacuum conduit (28) that is attached to a remote vacuum pressure source (150) of a conventional type. The needle (40) has a sharpened needle tip (152) adapted to penetrate or cut into tissue. Adjacent to the tip (152) is a tissue sample basket (154). Preferably, the sample basket (154) is provided with holes (156) for applying suction to a tissue sample received in the basket (154). The suction is provided through the vacuum tube (144).

The internal components described above are housed within the housing (12) and a proximal end cap (158) forms the proximal end (20) of the housing. A toggle nut stop (160) is used to limit proximal movement of the toggle nut (126) and, thus, the needle (40). Distal movement of the toggle nut (126) and the needle (40) are limited by the proximal face (162) of the gear case distal end (163). The gear case proximal end (164) comprises a plate having series of holes (168, 170, 172, 174). The gear case (66) is positioned in the housing (12) toward the proximal. A first, central hole (168) receives the vacuum tube (144) and needle (40).

The needle (40) extends through a central hole (176) in the distal end (162) of the gear case (66) and through a central hole (178) of the distal support (34). A radiolucent slide (180) having a central hole (182) aligned with the distal support central hole (178) is provided and receives the needle (40) therethrough. The slide (180) is fixed to the radiolucent tube (38) and enables it to be adjusted relative to the housing (12) in the axial direction in accordance with operation as described below.

The four remaining holes (168, 170, 172, 174) rotationally support, respectively, the needle drive gear (122), the master drive gear (78), the third cutter gear (76), and the cutter advance gear (94).

Operation

In operation, the tissue sampling device (10) is used to retrieve one or more tissue samples from a patient. In a biopsy retrieval operation, for example, it may be desired to take more than one tissue sample from a patient to locate one or more lesions.

During a tissue retrieval procedure such as a breast biopsy procedure, a patient is positioned on or next to a commercially available biopsy table or other positioning and imaging apparatus. Using conventional imaging technology, such as ultrasound, a physician locates a desired target area for tissue sample retrieval.

The device (10) may either be held in hand by a physician or it may be mounted to a cradle (14) which is mounted to a moveable carriage (184) as shown in FIG. 1. The carriage (184) is part of an imaging table or other commercially known positioning device. The device (10) has bearing grooves (186) designed to cooperate with the cradle (14) to hold the device (10) within the cradle (14) in a manner permitting rotational movement with little friction.

The initial step to obtaining a tissue sample requires introducing the needle tip (152) into and through the skin of the patient. The needle tip (152) may be advanced into and through the skin in one of two ways. A first way is to merely push the device forward by hand, using only manual force. The physician may monitor position during such introduction of the needle tip (152) using ultrasound imaging. Another way to advance the needle tip (152) into and through the skin is to advance a mechanical carriage (184) which holds the device (10) and thus the needle (152) relative therewith. Using imaging means or predetermined coordinates associated with carriage position, the needle tip (152) can be advance to a target zone.

Figure 4A:
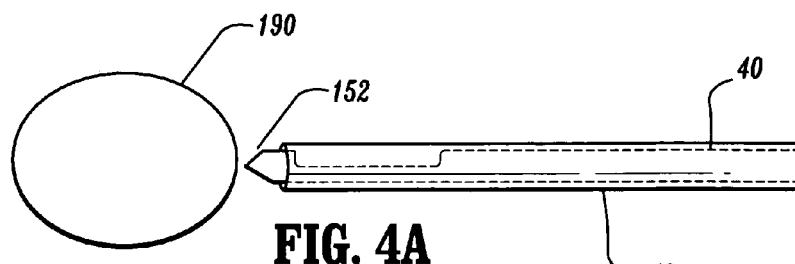
FIGS. 4A-4E are schematic side views of components of the device shown in FIG. 1 being operated in a manner according to a preferred embodiment of the present invention method.
Figure 4B:
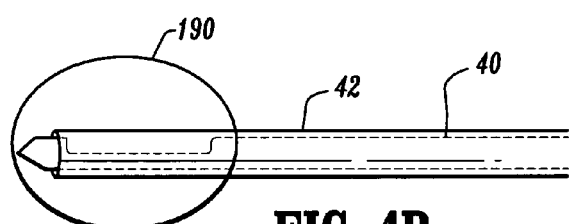

After introduction of the needle tip (152) into and through the skin, the needle tip (152) is advanced further by either of the means described in the preceding paragraph until the needle tip (152) is adjacent to the tissue sample target zone (190) as shown in FIG. 4A. Next, the needle tip (152) is advanced by either means so that the tissue sample receiving basket (154) is positioned within the target zone (190) as shown in FIG. 4B. Alternatively, the needle tip (152) may be advanced into the target zone (190) by the optional firing mode.

In the firing mode, the tip (152) is advanced relative to the housing (12) by a predetermined distance in a rapid fire manner so as to ensure cutting and penetration into a tissue region, rather than pushing the tissue out of the way of the needle tip (152). To facilitate rapid firing, a modular firing mechanism (192) having a spring-loaded firing hammer (194) is positioned with the hammer (194) in the firing port (196, FIG. 1) of the housing (12). The hammer (194) lines up proximally to the needle flange (136) so that when the firing mechanism (192) is fired by pulling its trigger (198), the hammer (194) pushes the flange (136) and needle tip (152) rapidly in the distal direction. It order to execute this firing mode, it is necessary that the flags (130, 132) are positioned so that the first flag (130) is positioned for alignment with the flange (136) while the second flag (132) is positioned out of alignment with the flange (136), as described above. This keeps the second flag (132) out of the way of the flange (136) during firing. The device (10) is preferably shipped in its original, unused state so that the flags (130, 132) are in the alignment described immediately above. If necessary, the position of the flags (130, 132) is controlled by rotating the leadscrew (124) in one direction or the other, as the toggle nut (126) engages the leadscrew (124) with enough friction to cause it to rotate with the leadscrew (124) for a limited rotational distance until it makes contact on either side and then the leadscrew (124) rotates relative to the toggle nut (126) to cause it to advance linearly along the leadscrew (124). Rotation of the leadscrew (124) may be caused by activating an electronic switch (200), which may be mounted on the housing (12) or remotely, to selectively activate a bi-directional, remote rotational motor (86). The motor (86) rotates the drive cable (80). As described above, the drive cable (80) is moved axially relative to the housing (12) by conventional means such as a solenoid or other type of linear actuator (88), which can be activated by an electronic switch (204) located on the housing (12) or remotely.

Figure 4C:
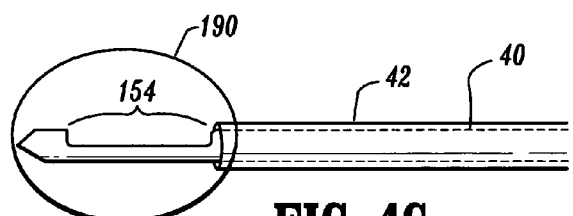
Figure 5:
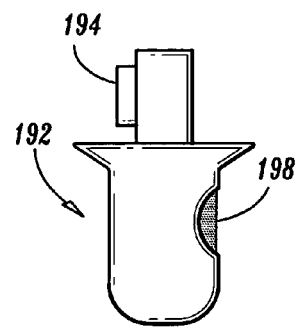
FIG. 5 is a schematic front view of an optional component according to a first embodiment of the present invention.

After the tissue sample receiving basket (154) is positioned within the target zone (190) as shown in FIG. 4B, the cutter (42) is moved back away from the needle tip (154) by mechanical components described above in order to expose the basket (154) to the tissue to be sampled as shown in FIG. 4C. The step of moving the cutter (42) may be initiated by activating an electronic switch (206) located on the housing (12) or located remotely. Once the basket (154) is exposed to the tissue sample target zone (190), suction may be applied through the holes (156) via the vacuum tube (144) and vacuum source (150) as described above. The vacuum pressure may be initiated by an electronic switch (208) located on the housing (12) or remotely. Shortly after vacuum pressure is activated, and tissue is drawn into the basket (154), the cutter (42) may be rotated and advanced linearly by mechanical means as described above until it reaches the position shown in FIG. 4D. The sequence of activating the vacuum and moving the cutter (42) may be initiated by a single electronic switch (210) located on the housing (12) or remotely.

Figure 4D:
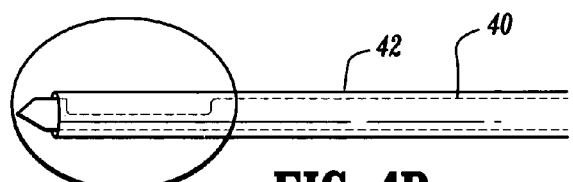
Figure 4E:
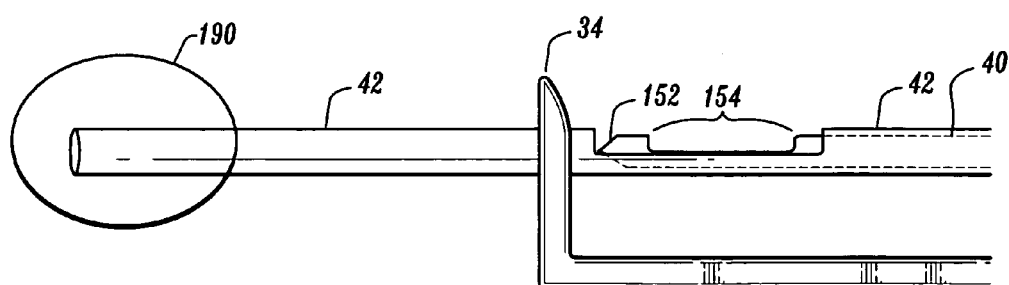

After the cutter (42) advances fully past the basket (154), as shown in FIG. 4D, a tissue sample will have been cut and captured in the basket (154). The cutter (42), now in a distally extended position, is stopped to hold the sample site and the needle (40) is retracted so that the basket (154) is positioned in the tissue specimen retrieval zone (36) as shown in FIG. 4E for removal of the tissue sample (212). The tissue sample (212) may be grasped or removed from the basket (154) by forceps or other known means.

If a subsequent sample is desired, the needle (40) is advanced by activating an electronic switch (214) which is located on the housing (12) or remotely which, in turn, activates the mechanical components as described above for linear advancement of the needle (40) using the leadscrew (124) and toggle nut (126). The needle tip (152) is advanced distally of the cutter (42) as shown in FIG. 4B. The device (10) can then be adjusted linearly or rotationally relative to the patient and the tissue target zone (190). The next sequence of retrieving a tissue sample may be initiated by moving the cutter (42) back away from the needle tip (152) in order to expose the basket (154). The vacuum, cutting and tissue sequences as described above are repeated to obtain another sample. The above described procedure can be repeated as many times as needed to obtain a desired number of samples.

Upon completion of removal of a desired number of tissue samples, the master drive gear (78) and drive cable (80) are detached from the device (10) so that the remainder of components of the device (10) can be discarded. The vacuum conduit (148) is removed from the vacuum source (150) and discarded along with the device (10). The drive cable (80) can be attached to a new device of the same type as the device (10) described herein and another vacuum conduit (148) can be attached between the device (10) and the vacuum source (150) for subsequent use with another patient.

If it is desired to reduce the length of the tissue area being sampled, the slide (180) fixed to the radiolucent tube (38) can be extended distally with respect to the housing (12) to a predetermined distance so as to partially block the sample basket (154) when the needle (40) is in an extended position. Because the tube (38) and slide (180) are radiolucent, neither will interfere with the ability to view the surrounding site during a procedure.

While the preferred embodiments of the invention have been disclosed and described herein, it is understood that variation and modification can be made without departing from the scope of the present invention claimed.

What is claimed is:

1. A tissue removal device for selectively removing one or more tissue portions from a medical patient, the device comprising:
   a housing;
   a cutter rotatably and axially slidably mounted within the housing, the cutter includes an elongated hollow tube having a distal end defining a cutting edge;
   a needle slidably disposed within the cutter, the needle includes a piercing tip and defines a tissue receiving section adjacent the piercing tip, the needle being configured to deliver suction to the tissue receiving section to draw a portion of tissue therein, wherein the cutter selectively severs the portion of tissue while it is held in the tissue receiving section; and
   a single drive cable operatively attached at one end to the housing, wherein the drive cable moves the cutter causing the cutter to sever the portion of tissue and selectively moves the needle relative to the housing.

2. The device according to claim 1, wherein the cutter includes a tissue sample retrieval window formed near a proximal end thereof.

3. The device according to claim 2, further comprising:
   a first cutter gear fixedly connected to a proximal end of the cutter for imparting rotation to the cutter.

4. The device according to claim 3, further comprising:
   an internal gear rotatably supported within the housing, the internal gear including internal gear teeth for engaging the first cutter gear, wherein the first cutter gear is adapted to translate longitudinally relative to the internal gear.

5. The device according to claim 4, further comprising:
   a master drive gear rotatably disposed within the housing and operatively connected to the drive cable;
   a cutter drive shaft including a distal end and a proximal end operatively connected to the master drive gear; and
   a third cutter gear operatively connected to the distal end of the cutter drive shaft, wherein the third cutter gear is operatively engaged with the internal gear teeth of the internal gear, and wherein rotation of the drive cable imparts rotation to the internal gear.

6. The device according to claim 5, further comprising:
   a cutter advance gear operatively disposed within the housing, the cutter advance gear being in operative engagement with the master drive gear when the master drive gear is in engagement with the third cutter gear;

a cutter advance shaft having a proximal end connected to the cutter advance gear and a distal end including a threaded section; and
a lead nut operatively disposed on the threaded section of the cutter advance shaft, the lead nut including an extension arm extending distally therefrom and which is in contact with a proximal face of the first cutter gear,
wherein as the cutter advance shaft rotates in a first direction, the lead screw translates distally, moving the first cutter gear in a distal direction relative to the internal gear.

7. The device according to claim 6, further comprising:
a biasing element operatively engaged with a distal face of the first cutter gear for exerting a proximally oriented force on the first cutter gear.

8. The device according to claim 7, further comprising:
a vacuum tube telescopically disposed within the needle, the vacuum tube having a proximal end attachable to a vacuum conduit for transmitting a vacuum from a vacuum source; and
wherein the tissue receiving section of the needle includes at least one hole formed therein for transmitting the vacuum from the vacuum source.

9. The device according to claim 8, further comprising:
a gear case disposed within the housing, the gear case includes a proximal end plate having a plurality of holes formed therein, wherein a central hole of the plurality of holes telescopically receives the needle therein, and the remaining holes of the plurality of holes rotationally support the master drive gear, the third cutter gear, and the cutter advance gear.

10. The device according to claim 1, further comprising:
a support extending distally from the housing, the support including a hole formed therein for receiving the needle therethrough, wherein the hole formed in the support is axially aligned with a longitudinal axis of the needle.

11. The device according to claim 10, further comprising:
a slide operatively connected to a distal end of the housing, the slide including a central hole axially aligned with the hole formed in the support; and
a radiolucent tube operatively connected to the slide.

12. The device according to claim 1, further comprising:
remote drive means connectable to the single drive cable, the remote drive means including a single rotational motor adapted to rotate in two directions.

13. A tissue removal device for selectively removing one or more tissue portions from a medical patient, the device comprising:
a housing;
a cutter rotatably and axially slidably mounted within the housing, the cutter includes an elongated hollow tube having a distal end defining a cutting edge;
a needle slidably disposed within the cutter, the needle includes a piercing tip and defines a tissue receiving section adjacent the piercing tip, the needle being configured to deliver suction to the tissue receiving section to draw a portion of tissue therein, wherein the cutter selectively severs the portion of tissue while it is held in the tissue receiving section;
a single drive cable operatively attached at one end to the housing, wherein the drive cable moves the cutter causing the cutter to sever the portion of tissue and selectively moves the needle relative to the housing; and
a vacuum tube telescopically disposed within the needle, the vacuum tube having a proximal end attachable to a vacuum conduit for transmitting a vacuum from a vacuum source.

14. The device according to claim 13, further comprising:
a slide operatively connected to a distal end of the housing, the slide including a central hole axially aligned with the hole formed in the support; and
a radiolucent tube operatively connected to the slide.

15. A tissue removal device for selectively removing one or more tissue portions from a medical patient, the device comprising:
a housing;
a cutter rotatably and slidably supported on the housing and extending from a distal end thereof, the cutter including a hollow tube defining a distal cutting edge and a tissue sample retrieval window formed near a proximal end thereof;
a needle telescopically disposed within the hollow tube of the cutter, the needle including a piercing tip formed at a distal end thereof and a tissue receiving section formed adjacent the piercing tip, the needle is configured to deliver suction to the tissue receiving section to draw a portion of tissue therein, wherein the cutter selectively severs the portion of tissue while it is held in the tissue receiving section,
wherein the needle and cutter are movable relative to one another between a position wherein the tissue sample retrieval window of the cutter is in registration with the tissue receiving section of the needle, and at least one other position wherein the tissue sample retrieval window of the cutter is out of registration with the tissue receiving section of the needle; and
a drive cable operatively attached at one end to the housing, wherein the drive cable moves the cutter causing the cutter to axially slide and rotate relative to the needle in order to sever the portion of tissue and to selectively axially move the needle relative to the housing to align the tissue receiving section of the needle with the tissue sample retrieval window of the cutter.

16. The device according to claim 15, further comprising:
a first cutter gear fixedly connected to a proximal end of the cutter for imparting rotation to the cutter; and
an internal gear rotatably supported within the housing, the internal gear including internal gear teeth for engaging the first cutter gear, wherein the first cutter gear is adapted to translate longitudinally relative to the internal gear.

17. The device according to claim 16, further comprising:
a master drive gear rotatably disposed within the housing and operatively connected to the drive cable;
a cutter drive shaft including a distal end and a proximal end operatively connected to the master drive gear; and
a third cutter gear operatively connected to the distal end of the cutter drive shaft, wherein the third cutter gear is operatively engaged with the internal gear teeth of the internal gear, and wherein rotation of the drive cable imparts rotation to the internal gear.

18. The device according to claim 17, further comprising:
a cutter advance gear operatively disposed within the housing, the cutter advance gear being in operative engagement with the master drive gear when the master drive gear is in engagement with the third cutter gear;
a cutter advance shaft having a proximal end connected to the cutter advance gear and a distal end including a threaded section; and
a lead nut operatively disposed on the threaded section of the cutter advance shaft, the lead nut including an extension arm extending distally therefrom and which is in contact with a proximal face of the first cutter gear, wherein as the cutter advance shaft rotates in a first direction, the lead screw translates distally, moving the first cutter gear in a distal direction relative to the internal gear.

19. The device according to claim 18, further comprising:
a biasing element operatively engaged with a distal face of the first cutter gear for exerting a proximally oriented force on the first cutter gear.

20. The device according to claim 15, further comprising:
a slide operatively connected to a distal end of the housing, the slide including a central hole axially aligned with the hole formed in the support; and
a radiolucent tube operatively connected to the slide.

\* \* \* \* \*